(12) United States Patent
Spangler

(10) Patent No.: US 12,296,344 B2
(45) Date of Patent: May 13, 2025

(54) TRANSPARENT HEATING ELEMENTS FOR POLYMERASE CHAIN REACTION DEVICES

(71) Applicant: Frank Leo Spangler, St. George, UT (US)

(72) Inventor: Frank Leo Spangler, St. George, UT (US)

(*) Notice: Subject to any disclaimer, the term of this patent is extended or adjusted under 35 U.S.C. 154(b) by 769 days.

(21) Appl. No.: 17/456,219

(22) Filed: Nov. 23, 2021

(65) Prior Publication Data

US 2022/0161264 A1 May 26, 2022

Related U.S. Application Data

(60) Provisional application No. 63/117,280, filed on Nov. 23, 2020.

(51) Int. Cl.
*B01L 7/00* (2006.01)
*C12Q 1/686* (2018.01)

(52) U.S. Cl.
CPC .......... *B01L 7/52* (2013.01); *B01L 2300/0663* (2013.01); *B01L 2300/1883* (2013.01); *B01L 2300/1894* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 8,088,616 B2* | 1/2012 | Handique | B01L 3/502738 435/287.1 |
| 9,399,219 B2* | 7/2016 | Spangler | B01L 7/5255 |
| 9,920,315 B2* | 3/2018 | Kartalov | C12Q 1/6853 |
| 2006/0068611 A1* | 3/2006 | Weaver | H10N 10/00 204/192.12 |
| 2015/0099644 A1 | 4/2015 | Chen et al. | |
| 2018/0070411 A1 | 3/2018 | Wei | |
| 2019/0263089 A1 | 8/2019 | Kotake et al. | |

* cited by examiner

*Primary Examiner* — Natasha E Young
(74) *Attorney, Agent, or Firm* — Gurr & Brande, PLLC; Robert A. Gurr

(57) ABSTRACT

A thermal array has a first heating element, a second, transparent heating element, a first insulator, a second insulator, and a cooling block. The transparent heating element is a layer of glass with one or more heating wires cast into, or coupled onto, the glass, or a thermo-resistive coating sputtered onto one side of the glass. The transparent heating element may further have a temperature sensor to monitor the temperature and thereby ensure that the layer of glass is held at a predetermined temperature. The thermal array includes bandpass light filters to be able to detect the exact fluorescence being produced.

19 Claims, 5 Drawing Sheets

TRANSPARENT HEATING ELEMENTS FOR POLYMERASE CHAIN REACTION DEVICES

CROSS-REFERENCE TO RELATED APPLICATIONS

This application claims the benefit of U.S. Provisional Application Ser. No. 63/117,280, filed on Nov. 23, 2020, which is incorporated herein by reference.

TECHNICAL FIELD

The present disclosure relates to biotechnology. More particularly, the present application relates to Polymerase Chain Reaction (PCR) devices.

BACKGROUND

The Polymerase Chain Reaction (PCR) allows scientists to make millions of copies of a sample of DNA. This technique has revolutionized many aspects of current research, including the diagnosis of genetic defects and the detection of infectious diseases such as the AIDS virus in human cells. Additionally, the technique is also used by criminologists to link specific persons to samples of blood or hair through DNA comparison.

PCR is the gold-standard used in molecular diagnostics. The powerhouse of PCR is real-time PCR (RT-PCR). This is where each cycle of PCR (there are typically 40 cycles per run) is measured for growth or amplification of PCR product. The amplification is an exponential process that produces billions of copies of product, making it one of the most sensitive technologies available to molecular diagnostics. In order to measure the PCR product, fluorescent molecules are added to the reaction mixture causing the reaction mixture to glow brighter and brighter as more and more PCR product is made. In order to detect that fluorescence, special circuitry has to be added.

The detection circuitry is built into the PCR machine, and this addition is what upgrades a standard PCR device to a RT-PCR device. A typical RT-PCR device will observe the fluorescence from above the reaction tube. The reaction tube will have some PCR chemistry in the bottom of it, and the fluorescent molecules will be in that chemistry. As PCR product is made, the amount of fluorescence will increase and thus produce a detection signal.

A more recent PCR device has been invented by the inventor hereof and is called the Thermal Array (see U.S. Pat. No. 9,662,653, titled "Thermal Array and Method of Use," and U.S. Pat. No. 9,399,219, titled "Thermal Array," both of which are incorporated herein by reference). The Thermal Array processes a PCR reaction much quicker than a standard PCR machine, but the Thermal Array does not allow the observation of fluorescence from above due to its novel way of processing a PCR reaction. It would be ideal to observe the reaction from the side of the Thermal Array; however, the side of the reaction vessel is in direct contact with a heating element of the Thermal Array, obstructing its view. A Thermal Array with the ability to observe fluorescent reactions would allow RT-PCR devices to be faster, less expensive, use less energy, and much more portable. Accordingly, there is a need for a Thermal Array that allows a user to observe the fluorescence reaction. The present disclosure seeks to solve these and other problems.

SUMMARY OF EXAMPLE EMBODIMENTS

In some embodiments, a thermal array comprises a first heating element, a second, transparent heating element, a first insulator, a second insulator, and a cooling block. The transparent heating element comprises a layer of glass with one or more heating wires cast into, or coupled onto, the glass, or applying voltage to a thermo-resistive coating applied onto one side of the glass. The transparent heating element may further comprise a temperature sensor to monitor the temperature and thereby ensure that the layer of glass is held at a predetermined temperature. The thermal array may comprise bandpass light filters to be able to detect the exact fluorescence being produced.

DETAILED DESCRIPTION OF EXAMPLE EMBODIMENTS

Figure 1:
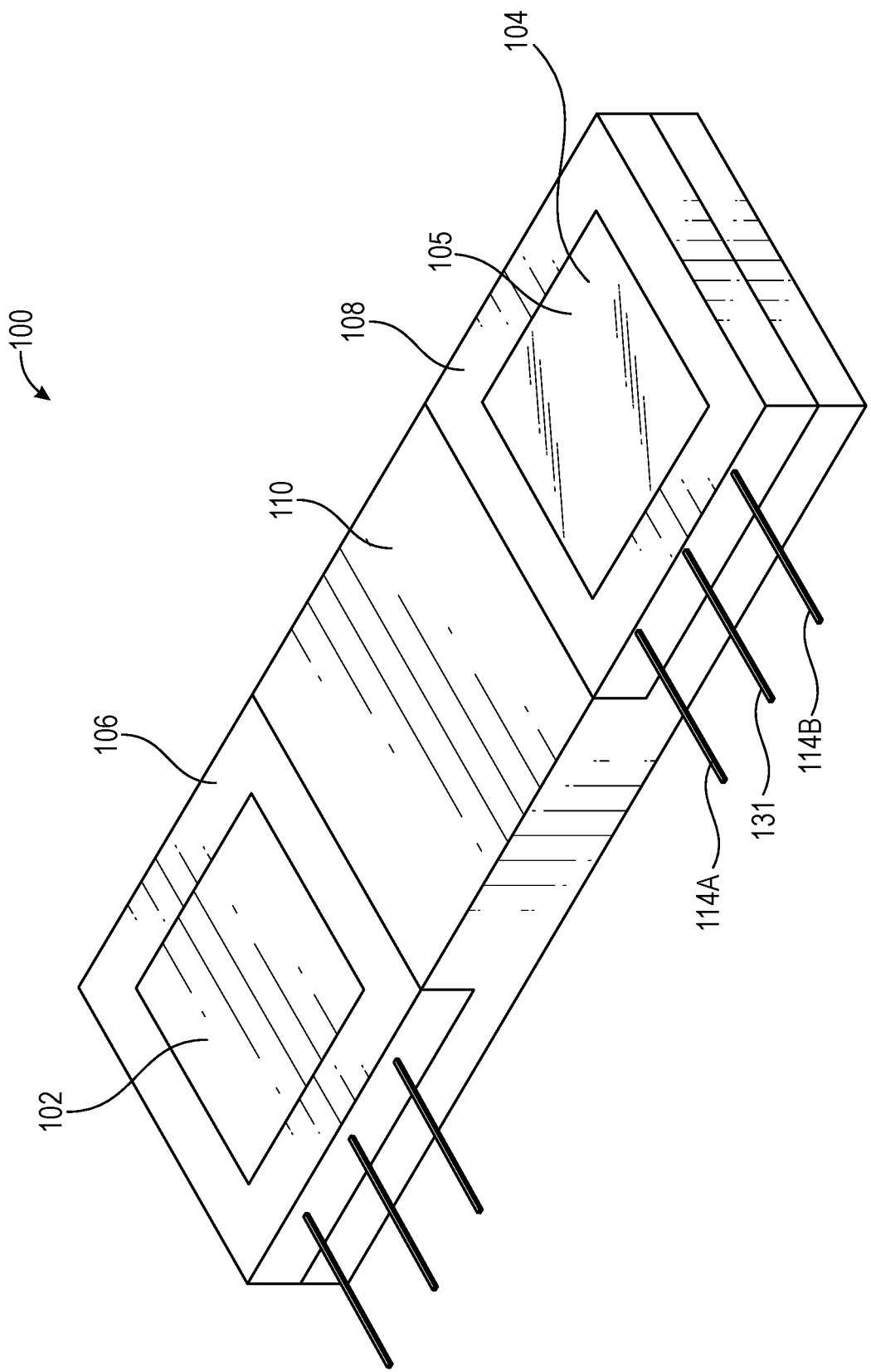
FIG. 1 illustrates a front, bottom perspective view of a thermal array.
Figure 2:
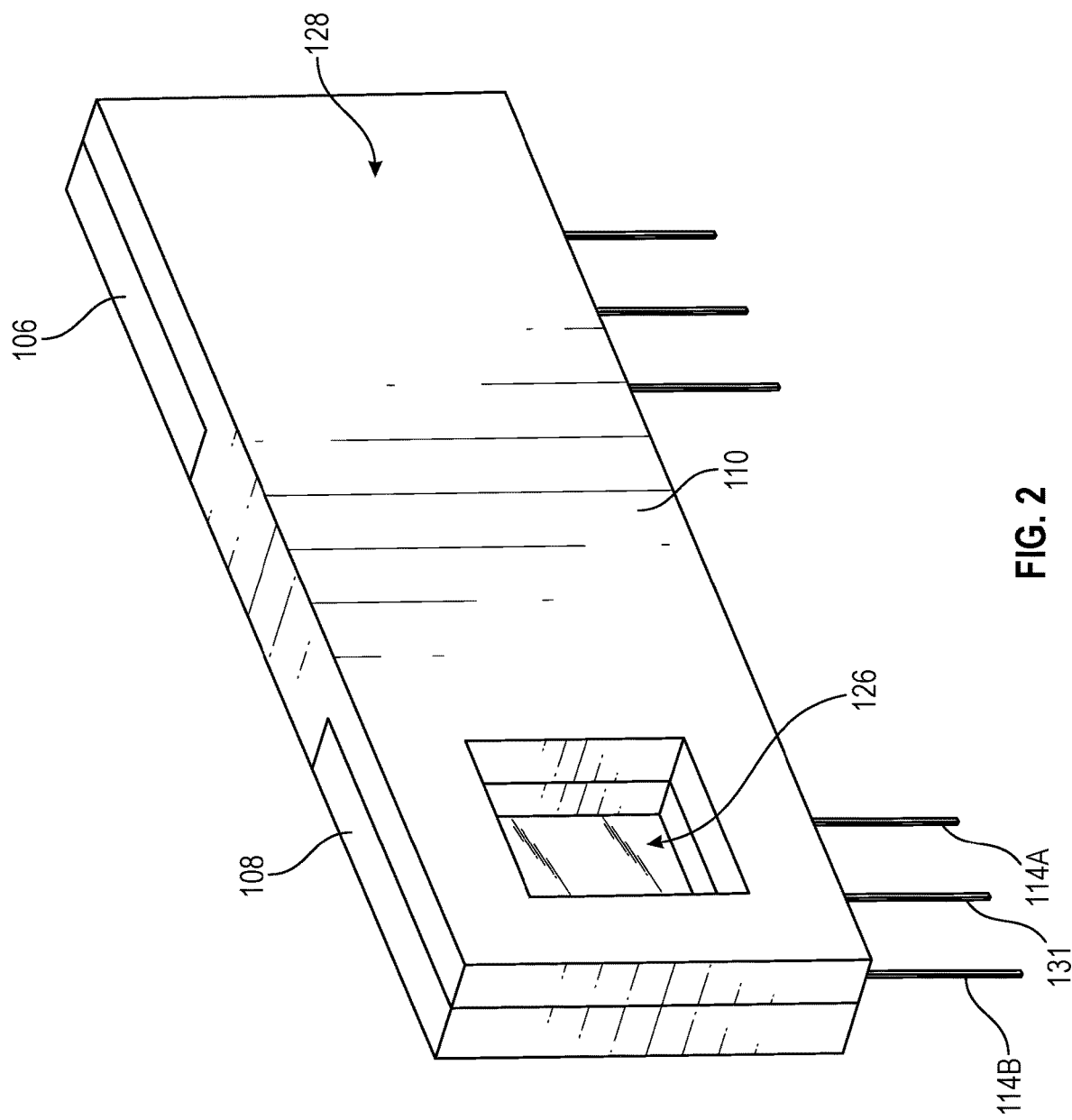
FIG. 2 illustrates a back, side perspective view of a thermal array.
Figure 3:
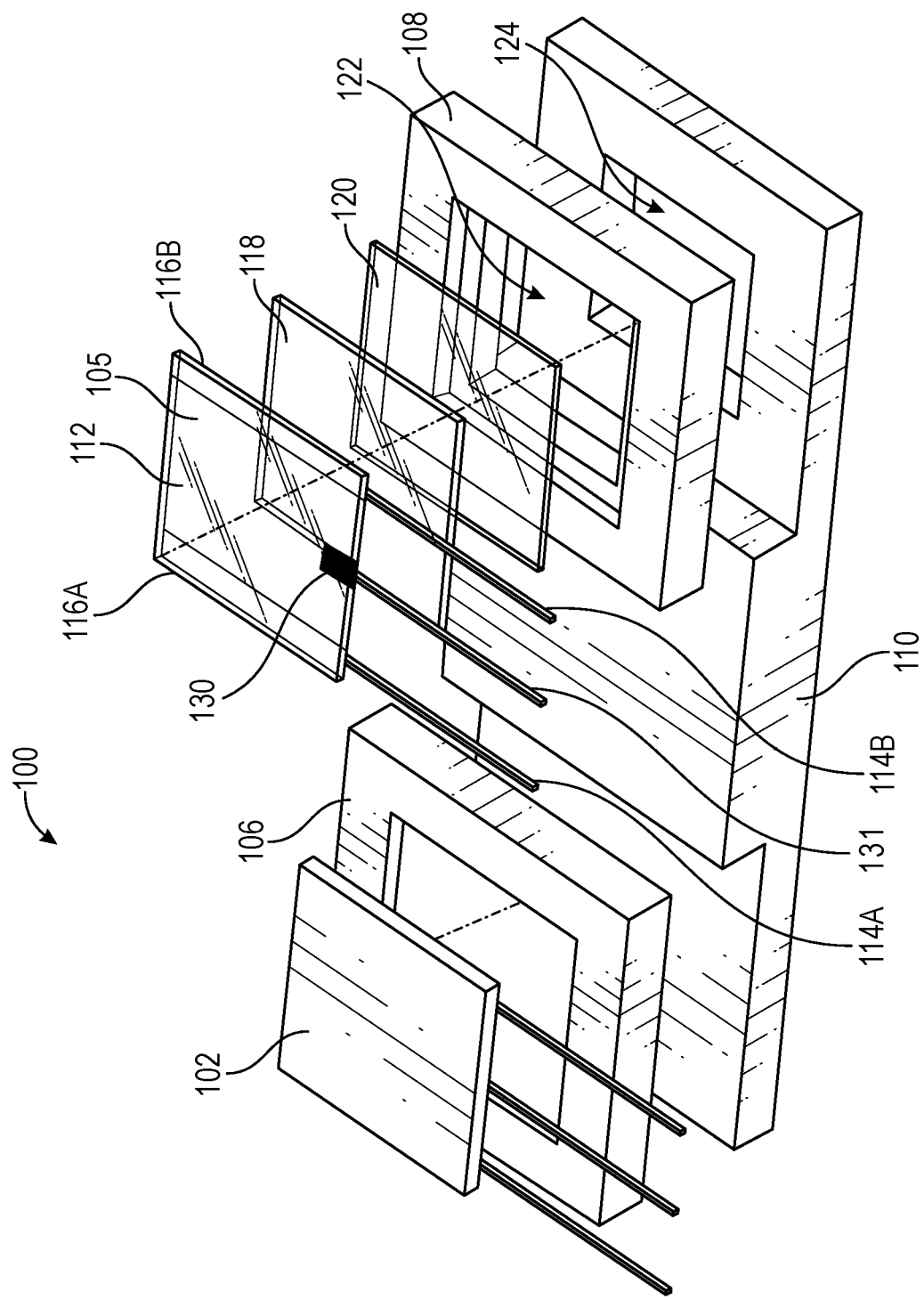
FIG. 3 illustrates a front, bottom exploded view of a thermal array.
Figure 4:
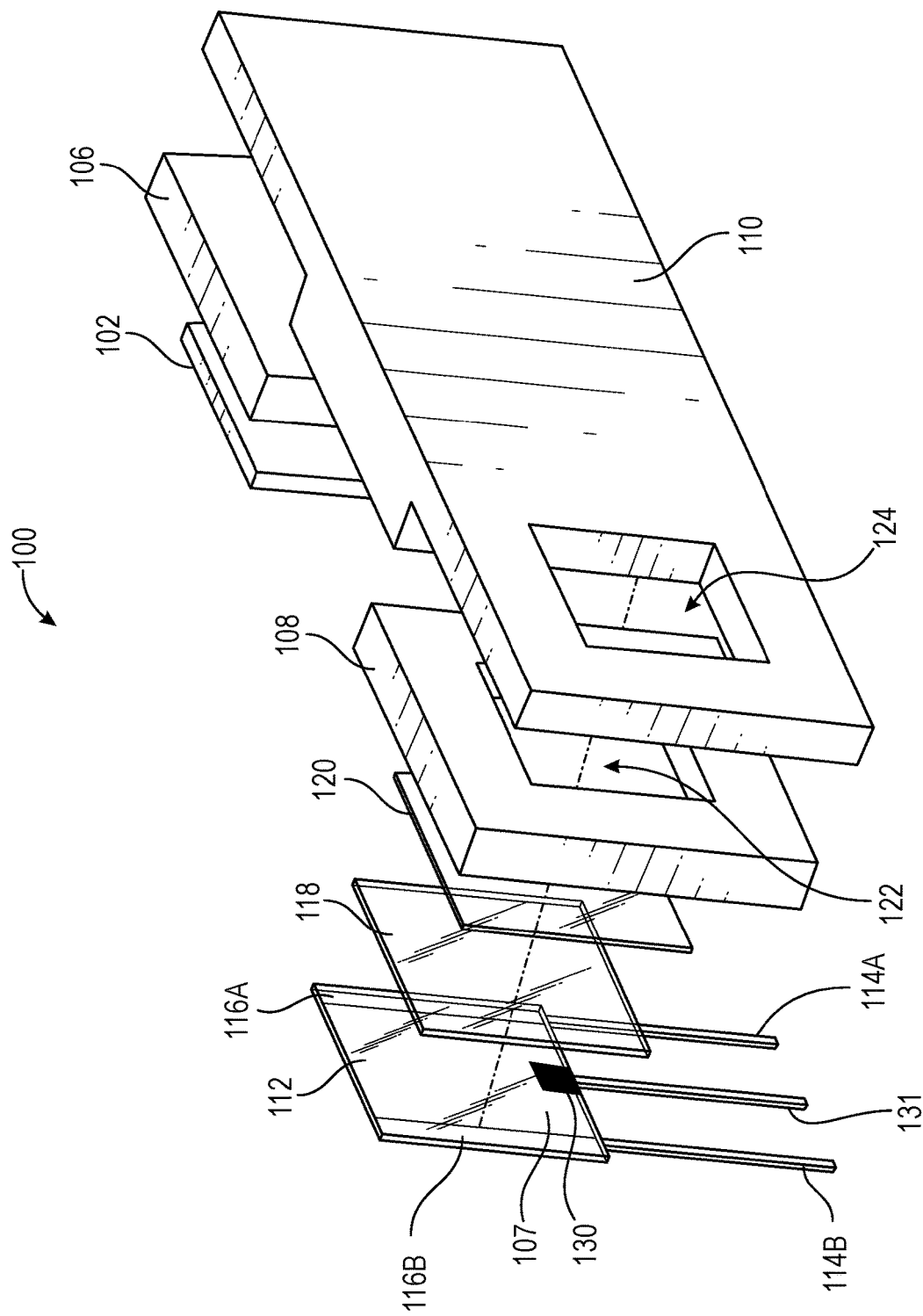
FIG. 4 illustrates a back, side exploded view of a thermal array.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

As previously discussed, there is a need for a thermal array that is capable of performing both amplification and detection simultaneously. The thermal array comprising a transparent heating element disclosed herein solves this problem and other problems.

In some embodiments, as shown in FIGS. 1-4, a thermal array 100 comprises a first heating element 102, a second, transparent heating element 104, a first insulator 106, a second insulator 108, and a cooling block 110. The transparent heating element 104 comprises a first transparent layer 112 (e.g., glass) with one or more heating sources, such as heating wires 114A-B (e.g., nichrome wires) cast into and/or coupled onto the first transparent layer 112, or applying voltage to a transparent thermo-resistive coating (e.g., indium-tin oxide coating) applied onto one side of the first transparent layer 112. For example, in some embodiments, an adhesive film 116A-B may be used to adhere the wires 114A, 114B to the first transparent layer 112. A first side 105 of the first transparent layer 112 remains exposed so as to contact a sample vessel (discussed more later herein). A second side 107 (FIG. 4) of the first transparent layer 112 is proximal to a second transparent layer 118 (e.g., glass).

The second transparent layer 118 is an insulating layer and is ideally dual pane with an air gap between the panes so as to function as an insulator to reduce the heat transference. While the second transparent layer 118 is described above as being dual pane, the present invention is not so limited. For example, the second transparent layer 118 may be a single pane comprising a transparent insulation, like aerogel or other known insulators. The second transparent layer 118 may be proximal to a light filter 120. In other words, the second transparent layer 118 is interposed between the first transparent layer 112 and the light filter 120 (e.g., bandpass light filter), the second transparent layer 118 functioning as an insulator to reduce heat transmission from the first transparent layer 112 to the light filter 120. It will be appreciated that while the second transparent layer 118 is described herein as an insulator, other insulating methods may be used, such as applying aerogel to the second side 107 of the first transparent layer 112.

A combination of insulators may be used as well, such as applying aerogel to the first transparent layer 112 and/or to additional transparent layers, such as the second transparent layer 118. By applying aerogel to the second side (and optionally insulating the 4 edges (or plurality of edges, depending on the form factor of the layer) with transparent or opaque insulation) of the first transparent layer 112, heat is directed outwardly on the first side 105 toward the sample vessel. While the light filter 120 is shown as coupled within the second insulator 108, it is not required. In some embodiments, the light filter may be coupled to an optical detection device external to the transparent heating element 104. In some embodiments, the light filter 120 may be replaced with an additional pane with either an air gap or insulation. In other words, the transparent heating element 104 may comprise, in some embodiments, a first transparent layer 112 with transparent insulation applied thereon; may comprise a second transparent layer 118; and/or, may comprise a third transparent layer 120 which may or may not also function as a light filter.

The first transparent layer 112, second transparent layer 118, and light filter 120 are all received within (e.g., set within or manufactured within) the second insulator 108, the second insulator 108 comprising a second insulator viewing aperture 122 in the center thereof and being coupled to the cooling block 110. The first insulator 106 and second insulator 108 can be made of typical insulative materials such as fiberglass, expanding spray foam, aerogel, or any equivalent. The first and second insulators 106, 108 help prevent heat energy loss into other components of the thermal array 100 and the environment. The cooling block 110 may be made from aluminum alloy, copper, some combination thereof, or any other material known in the art that functions well as a heat sink (i.e., draws heat from the source).

The cooling block 110 comprises a cooling block viewing aperture 124 that is aligned with at least a portion of the second insulator viewing aperture 122. As a result, when viewed from the back side (FIG. 2), because the first transparent layer 112, second transparent layer 118, and light filter 120 are all transparent (e.g., glass), the fluorescence reaction may be observed through the cooling block viewing aperture 124 and second insulator viewing aperture 122. The light filter 120 allows a user to detect the exact fluorescence being produced. While glass is described for the transparent layers, it will be appreciated that crystals, polymers, and any other transparent material may be used as long as it is capable of maintaining its shape when heated and is capable of conducting heat into the sample vessel.

An optical detection device may be configured to make measurements through the window 126 (defined as the first transparent layer 112, second transparent layer 118, transparent light filter 120, cooling block viewing aperture 124, and second insulator viewing aperture 122) from the back side 128 of the thermal array 100. In other words, the optical detection device measures levels of fluorescence being produced in a sample vessel. The optical detection device may be any such device known in the art, such as, but not limited to, a photo sensor using either a Light Detection Resistor (LDR) or Photodiode circuit, an optional amplification circuit, and an analog to digital converter. In some embodiments, a heat sink may be coupled to the optical detection device as well so as to maintain a cool operating temperature.

The transparent heating element 104 may further comprise a temperature sensor 130 (e.g., thermocouple, digital thermal sensor, etc.) and wire 131 coupled thereto to monitor the temperature of the first transparent layer 112 and thereby ensure that the first transparent layer 112 is held at a predetermined temperature.

Figure 5:
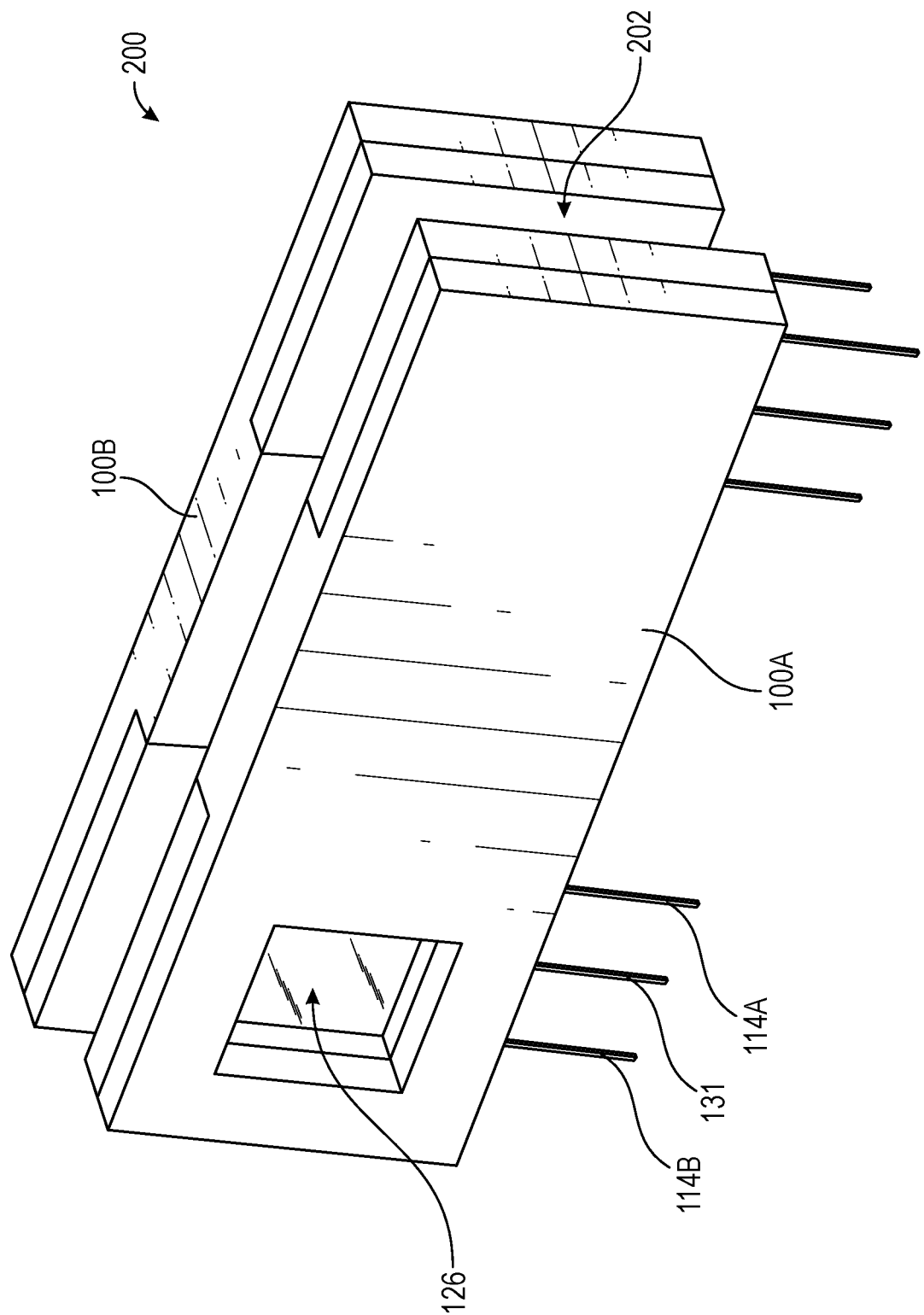
FIG. 5 illustrates a perspective view of a thermal array system.

Accordingly, as shown in FIG. 5, a thermal array system 200 comprises a first thermal array 100A and a second thermal array 100B arranged in a mirror image to one another and forming a conductive channel 202. A sample vessel is configured to pass through the conductive channel 202 and be in physical contact with both the first thermal array 100A and second thermal array 100B at the same time. While both thermal arrays 100A, 100B may have a window 126, it is not required, and only one thermal array 100A needs to have a window 126. Accordingly, a user may perform PCR using the thermal array system 200, which is much more efficient and faster than standard PCR devices in the art, as described in U.S. Pat. No. 9,662,653, titled "Thermal Array and Method of Use," and U.S. Pat. No. 9,399,219, while also performing RT-PCR by measuring fluorescence through the one or more windows 126, drastically improving the speed over traditional RT-PCR.

The thermal array 100 can easily be powered by an AC to DC power supply in the 6-18 volt range. Further in a preferred implementation, because of the greater efficiency of a thermal array 100, the thermal array 100 can function using batteries that can be recharged by an AC to DC power supply. Further, the thermal array system 200 can easily be moved out into the field to locations where services are needed—sometimes called point-of-care (POC) or point-of-service (POS). Further, the embodiments disclosed herein eliminate ramp times during a PCR run so the overall run times can be less than 8 minutes, versus the 60 minutes or so that is typical of conventional PCR devices currently known in the art. Further, the simplification of the technology allows the thermal array 100 as disclosed herein to be manufactured far below the costs of traditional PCR devices.

As disclosed herein, the cooling block 110 can be either passive or made active by chilling it with various refrigeration technologies, such as, by way of example only, a Peltier element or cooling fins, with or without a fan blowing over the fins. Fins are well known in the art and used frequently with heat sinks on computer CPUs and other heat sensitive components. Further, additional heating elements or cooling blocks may be added to the thermal array 100 as needed (i.e., not limited to two heating elements 102, 104).

It will be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A transparent heating element for use with a thermal array, the transparent heating element comprising:
   a first transparent layer comprising a first side, a second side, a plurality of edges,
   and one or more heating sources;
   wherein the first side remains exposed to conduct heat, the second side comprises transparent insulation, and the plurality of edges comprise insulation.

2. The transparent heating element of claim 1, further comprising a second transparent layer for insulation proximal to the second side of the first transparent layer.

3. The transparent heating element of claim 1, further comprising a transparent light filter.

4. The transparent heating element of claim 1, wherein the first and second transparent layers are glass.

5. The transparent heating element of claim 1, further comprising a temperature sensor.

6. The transparent heating element of claim 1, wherein the transparent insulation comprises aerogel.

7. The transparent heating element of claim 1, wherein the heating sources comprise heating wires.

8. The transparent heating element of claim 1, wherein the heating sources comprise a transparent thermo-resistive coating.

9. A thermal array system, comprising:
   a first thermal array opposite a second thermal array creating a conductive channel, wherein at least one of the first and second thermal arrays comprises a window for viewing a fluorescent reaction in a sample vessel; and
   the sample vessel receivable within the conductive channel that is proximate to,
   and in contact with, each thermal array;
   wherein the window comprises:
      a cooling block viewing aperture;
      an insulator viewing aperture;
      a transparent insulating layer; and
      a transparent layer comprising at least one heating source.

10. The thermal array system of claim 9, wherein the heating source comprises heating wires.

11. The thermal array system of claim 9, wherein the heating source comprises a transparent thermo-resistive coating.

12. The thermal array system of claim 9, further comprising an optical detection device for measuring the fluorescent reaction through the window.

13. A thermal array, comprising:
   a first heating element coupled to a first insulator, the first insulator coupled to a cooling block on a first end;
   a second, transparent heating element coupled to a second insulator, the second, transparent insulator coupled to the cooling block on a second end; and
   a window for viewing a fluorescent reaction in a sample vessel in contact with the second, transparent heating element.

14. The thermal array of claim 13, wherein the window comprises:
   a cooling block viewing aperture; and
   an insulator viewing aperture.

15. The thermal array of claim 13, wherein the second, transparent heating element comprises one or more heating wires.

16. The thermal array of claim 13, wherein the second, transparent heating element comprises a transparent thermo-resistive coating.

17. The thermal array of claim 13, wherein the second, transparent heating element comprises glass.

18. The thermal array of claim 13, wherein the second, transparent heating element comprises crystal.

19. The thermal array of claim 13, wherein the second, transparent heating element comprises a polymer.

* * * * *